(12) United States Patent
Li et al.

(10) Patent No.: US 10,213,368 B2
(45) Date of Patent: Feb. 26, 2019

(54) ORAL CARE COMPOSITIONS

(71) Applicant: The Procter & Gamble Company, Cincinnati, OH (US)

(72) Inventors: Xiaoxiao Li, Beijing (CN); Yujun Li, Beijing (CN); Ross Strand, Beijing (CN); Andrew Frederic Broth, Mason, OH (US); William Michael Glandorf, Mason, OH (US); Steven Carl Burgess, Cincinnati, OH (US); Xiujun Xu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/633,389

(22) Filed: Feb. 27, 2015

(65) Prior Publication Data

US 2015/0320655 A1    Nov. 12, 2015

(30) Foreign Application Priority Data

May 7, 2014    (CN) ................. 2014/076944

(51) Int. Cl.
*A61K 8/19* (2006.01)
*A61K 8/73* (2006.01)
*A61Q 11/00* (2006.01)

(52) U.S. Cl.
CPC .................. *A61K 8/19* (2013.01); *A61K 8/73* (2013.01); *A61Q 11/00* (2013.01); *A61K 2800/30* (2013.01); *A61K 2800/48* (2013.01); *A61K 2800/52* (2013.01)

(58) Field of Classification Search
USPC ............................................. 424/49, 51, 575
See application file for complete search history.

(56) References Cited

U.S. PATENT DOCUMENTS

| 4,569,838 A | * | 2/1986 | de Vries ................... A61K 8/26 424/49 |
| 2010/0135928 A1 | * | 6/2010 | Baig ........................ A61K 8/25 424/51 |

FOREIGN PATENT DOCUMENTS

| WO | WO 2008/41055 | 4/2008 |
| WO | WO 2010/114546 | 10/2010 |

* cited by examiner

*Primary Examiner* — Walter E Webb
(74) *Attorney, Agent, or Firm* — Parker D. McCrary; James E. Oehlenschlager; Alexandra S. Anoff

(57) ABSTRACT

Oral care composition comprise a stannous ion source and a thickener consisting essentially of carrageenan and xanthan gum. A method for treating the oral cavity comprises administering the composition to the oral cavity in a toothpaste.

14 Claims, 1 Drawing Sheet

ORAL CARE COMPOSITIONS

CROSS REFERENCE TO RELATED APPLICATION

This application claims the benefit of Application No. CN2014/076944 filed May 7, 2014.

FIELD OF THE INVENTION

The present invention relates to oral care compositions containing stannous ions.

BACKGROUND OF THE INVENTION

Tin (II) (stannous) ions (i.e., stannous chloride) are added to oral care compositions to deliver multiple benefits including, for example: anti-microbial effects, control of breath malodor, control of dental plaque growth and metabolism, and reduced gingivitis. However, oral care compositions containing stannous chloride, especially in combination with thickening agents such as carboxymethyl cellulose (CMC), can suffer from poor rheological properties.

One of the main reasons for the problem is that $Sn^{2+}$ ion is prone to oxidation towards $Sn^{4+}$ causing the oral care composition to exhibit an unacceptably low viscosity. If a formulation routinely decreases in viscosity, such oral care composition can lack phase stability and tends to undergo phase separation over time or physical degradation of the structure. The problem is especially noticeable at the tip of the dispenser due to higher levels of oxygen penetrating the container from the exterior and reacting with the oral care composition closest to the tip.

As a result, consumer dissatisfaction will likely result as the oral care composition nearest the tip will be dispensed first from the dispenser and appear watery as the liquid has separated from the body of the composition. Various formulation approaches have been tried to stabilize stannous chloride containing oral care composition. PCT Publication No. WO2008/41055 (P&G) discloses stannous chloride containing oral care compositions. The composition examples include carboxymethyl cellulose (CMC). PCT Publication No. WO2010/114546 (Colgate-Palmolive) discloses dentrifice compositions comprising polysaccharide thickeners having xanthan gum and hydroxyethyl cellulose (HEC) for decreasing the viscosity of the toothpaste.

Despite the foregoing, there is still a need for stannous ions containing oral care compositions having improved phase stability and/or shelf-life stability over time (greater than 4 months to 24 months), at ambient conditions.

SUMMARY OF THE INVENTION

In one aspect, the present invention is directed to oral care compositions comprising: (a) from 0.01% to 5% of a stannous ion; (b) a thickener consisting essentially of: i) a carrageenan; and ii) a xanthan gum; and (c) at least 30% of a total water content; wherein the oral care composition has a pH of greater than 4 and is substantially free of a charged cellulose derivative having greater than 0.5 charged groups per sugar residue unit along the polysaccharide backbone. This minimizes cost and complexity to the formulation.

In another aspect, the present invention relates to a method for treating the oral cavity comprising administering to the oral cavity an oral care composition as described herein above.

One aim of the present invention is to provide an oral care composition, as described herein above, which can exhibit good rheological properties.

Another aim of the present invention is to provide such an oral care composition, as described herein above, with robust 'Tip Viscosity' which permits the composition to exhibit sufficient phase stability such that it does not phase separate after 4 months, preferably after 6 months, more preferably after 12 months, or even more preferably after 24 months, at ambient conditions.

A further aim of the present invention is to provide such an oral care composition, as described herein above, without a significant variation in the 'Tip Viscosity' of the oral care composition after 4 months, preferably after 6 months, more preferably after 12 months, or even more preferably after 24 months, at ambient conditions.

A yet further aim of the present invention is to provide such an oral care composition, as described herein above, which tends not to exhibit substantial decreases in 'Tip Viscosity' after 4 months, preferably after 6 months, more preferably after 12 months, or even more preferably after 24 months, at ambient conditions.

These and other features, aspects, and advantages of the present invention will become evident to those skilled in the art from the detailed description which follows.

BRIEF DESCRIPTION OF THE DRAWINGS

While the specification concludes with claims that particularly point out and distinctly claim the invention, it is believed the present invention will be better understood from the following description of the accompanying figures.

DETAILED DESCRIPTION OF THE INVENTION

Definitions

Figure 1:
FIG. 1 is a photo of a $SnCl_2$ and carboxymethyl cellulose (CMC) containing oral care composition that has undergone phase separation due to oxidation reaction.

As used herein, the term "average molecular weight" refers to the average molecular weight as determined using gel permeation chromatography according to the protocol found in *Colloids and Surfaces A. Physico Chemical & Engineering Aspects*, Vol. 162, 2000, pg. 107-121. Unless otherwise specified, all molecular weight values herein refer to the weight average molecular weight and expressed in g/mol.

As used herein, the term "average degree of polymerization" (ADP) refers to the average degree of polymerization as determined by n, which refers to the number of anhydroglucose units (which are joined through 1,4 glucosidic linkages in cellulose structure) or the degree of polymerization (DP). ADP is calculated using the protocol found in Intrinsic Viscosity and Overall Rate, *Journal of Polymer Science*, Vol. 56, 1962, pg. 233-243.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "oral care composition" as used herein means a product that in the ordinary course of usage is retained in the oral cavity for a time sufficient to contact some or all of the dental surfaces and/or oral tissues for purposes of oral activity. In one embodiment, the composition provides a benefit when used in the oral cavity. The oral care composition of the present invention may be in various forms including toothpaste, dentifrice, tooth gel, tooth powders, tablets, rinse, sub gingival gel, foam, mouse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for direct application or attachment to oral surfaces, or incorporated into floss.

The term "orally acceptable carrier" as used herein means a suitable vehicle or ingredient, which can be used to form and/or apply the present compositions to the oral cavity in a safe and effective manner.

The term "dentifrice" as used herein means paste, gel, powder, tablets, or liquid formulations, unless otherwise specified, that are used to clean the surfaces of the oral cavity.

The terms "phase stable" and "phase stability" are used interchangeably and refer to the oral care composition visually (i.e., to the unaided eye) having no liquid separation from the composition's body over a defined period of time (under ambient conditions). In other words, phase stable oral care compositions of the present invention can resist syneresis.

The terms "shelf-life stable" and "shelf-life stability" are used interchangeably and refer to the oral care composition being deemed consumer acceptable after a defined period of time after its production (under ambient conditions). The test to determine this is by inverting the dispenser containing the oral care composition and holding it vertically for 10 seconds during which oral care composition should not drip out of the dispenser.

The term "substantially free" as used herein refers to no intentional amount of that material is added to the composition or an amount of a material that is less than 1%, 0.5%, 0.25%, 0.1%, 0.05%, 0.01%, or 0.001% of the composition.

The term "teeth" as used herein refers to natural teeth as well as artificial teeth or dental prosthesis.

The term "Tip Viscosity" as used herein means the viscosity of the oral care composition expressed in Pa·s and measured at or near the tip portion of the dispenser in which the composition is contained. The Tip Viscosity is determined according to the Tip Viscosity Assay as disclosed herein in the Test Methods Section.

The term "total water content" as used herein means both free water and water that is bound by other ingredients in the oral care composition.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Specifically, the present invention provides an oral care composition comprising:
  a. from 0.01% to 5% of stannous ions;
  b. a thickening agent consisting essentially of:
    i) from 0.65% to 5% of a carrageenan; and
    ii) from 0.3% to 5% of a xanthan gum; and
  c. at least 30% of a total water content;
wherein the composition has a pH greater than 4 and is substantially free of a charged cellulose derivative having greater than 0.5 charged groups per sugar residue unit along the polysaccharide backbone.

Stannous Ions

Stannous ions are used in oral care compositions to deliver benefits such as, for example, enamel care and cavity protection. Suitable stannous sources include stannous chloride, stannous fluoride, stannous acetate, stannous gluconate, stannous oxalate, stannous sulfate, stannous lactate and stannous tartrate. Preferably, the stannous salt is stannous chloride (i.e., $SnCl_2$) and may include stannous chloride dehydrate, stannous chloride anhydrous, and combinations thereof. Alternatively, the use a combination of stannous salts (e.g., stannous chloride and stannous fluoride) whereby both the desired stannous and fluoride ion are supplied through these salt combinations. The oral care compositions of the present invention may contain stannous ions in the amount ranging from 0.01% to 5% (100 to 50,000 ppm), 0.05% to 4% (500 to 40,000 ppm), or 0.075% to 3% (750 to 30,000 ppm). Preferably, such oral care compositions contain from 0.1% to 2% (1,000 to 20,000 ppm), from 0.5% to 1.5% (5,000 to 15,000 ppm), or from 0.2% to 0.7% (2,000 to 7,000 ppm) stannous ions.

The present invention is based on the observation that oral care compositions containing stannous ions (e.g., $SnCl_2$) in combination with certain thickening agents, such as charged cellulose derivatives like carboxymethyl cellulose (CMC), suffer from a decrease in viscosity of the composition near the tip of the dispenser. Over time this leads to the liquid separating from the body of the composition and a phase stability problem (see FIG. 1). This problem is most noticeable near the tip of the dispenser because oxygen can slowly penetrate through the crimped portions of the dispenser from the exterior and react with the unbound Sn ions in the formulation, as follows:

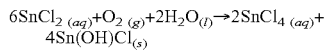

$$6SnCl_{2\ (aq)} + O_{2\ (g)} + 2H_2O_{(l)} \rightarrow 2SnCl_{4\ (aq)} + 4Sn(OH)Cl_{(s)}$$

CMC is an anionic polysaccharide commonly used as a structurant material in oral care compositions. The carboxyl group of the CMC reacts with the divalent ions (e.g., $Sn^{2+}$) to form cross-linked gels and provide sufficient viscosity and phase stability benefits to the compositions. Without wishing to be bound by theory, it is believed that the higher valent ion (e.g., $Sn^{4+}$) precipitate formed when the stannous oxidization occurs near the tip can inhibit the CMC gel hydration. As a consequence, the viscosity of the composition near the tip of the dispenser (referred to as 'Tip Viscosity') drops and the composition becomes thinner and more watery (also known as 'phase separation'). Applicants have surprisingly discovered an improved thickener system, as described herein below, for use in stannous ions containing oral care compositions to avoid, or at least mitigate, aid to reduce and/or eliminate the Tip Viscosity drop and/or phase stability problem near the tip of the dispenser.

Thickening Agents

The oral care compositions herein may include one or more thickening agents or binders to provide a number of benefits such as, for example, a desirable consistency of the oral care composition, desirable active release characteristics upon use, acceptable shelf-life stability (greater than 4 months to 24 months, or longer), acceptable phase stability (greater than 4 months to 24 months, or longer), and/or acceptable Tip Viscosity (greater than 100 P·s after 4.5 months at 40° C.) of the oral care composition.

Thickeners are present in the oral care compositions in the range from about 0.01% to about 15%, or from about 0.05% to about 10%, or from about 0.075% to about 7.5%. Preferably, such oral care compositions contain from about 0.1% to about 5%, or from about 0.5% to about 3%, or from about 0.75% to about 2%, thickeners.

The thickeners of the present invention consist essentially of a carrageenan and a xanthan gum. In an embodiment, the carrageenan is present in the oral care composition in the range from 0.65% to 5%, or from 0.75% to 4%, or from 1% to 3%, or from 1.25% to 2%. In another embodiment, the carrageenan may be selected from the group consisting of Kappa-carrageenan, Iota-carrageenan, Lambda-carrageenan, and combinations thereof. Preferably, the carrageenan is Iota-carrageenan. In another embodiment, the xanthan gum is present in the oral care composition in the range from 0.3% to 5%, from 0.5% to 4%, or from 0.75% to 3%.

The oral care composition of the present invention is substantially free of a charged cellulose derivative having greater than 0.5 charged groups per sugar residue unit along the polysaccharide backbone. In an embodiment, the oral care composition is substantially free of a charged cellulose derivative having greater than 0.6, or greater than 0.7, or greater than 0.8 charged groups per sugar residue unit along the polysaccharide backbone. A specific example of such a charged cellulose derivative is carboxymethyl cellulose (CMC).

Applicants have found that the use of a thickening agent having a lower concentration of reactive groups (e.g., carboxylate groups) means that there are fewer sites for cross-linking between the thickener and the stannous ions. For example, both CMC and xanthan gum contain carboxylate groups along their backbones. However, the density of charged carboxylate groups along the backbone for each polysaccharide is quite different. For instance, one commercially available form of CMC (CMC 2000S available from CPKelco) has a degree of substitution of about 0.9 carboxylate groups per sugar residue. In contrast, xanthan gum has a degree of substitution of less than 0.4 carboxylate groups per sugar residue.

Without wishing to be bound by theory, Applicants believe the degree of substitution with reactive groups has an impact on the rheology of the resultant composition. For instance, $Sn^{2+}$ complexes with the carboxylate groups to form ionic cross-links or bridges in-between two opposing carboxylate groups found on CMC or xanthan gum to form large networks that can increase viscosity of the compositions. Since the loss of free Sn ions due to the oxidation reaction with $O_2$ and $H_2O$ near the tip of the container will impact this ionic bridging and because there is less potential for ionic bridging for polysaccharides having less than 0.5 charged groups per sugar residue, Applicants have substituted xanthan gum for CMC in order to ensure robust Tip Viscosity of the composition despite the loss of $Sn^{2+}$ due to oxidation.

pH

The pH of the oral care composition is greater than 4. Preferably, the pH may be between 4.5 to 9.5, more preferably from 5 to 7, alternatively greater than 6, alternatively greater than 7, alternatively from 8 to 9, or combinations thereof. The pH is typically measured using a ratio of 1:3 of paste:water. For example, whereby 1 gram of the oral care composition (e.g., toothpaste) is mixed into 3 grams of deionized water, and then the pH with an industry accepted pH probe that is calibrated under ambient conditions. The pH is measured by a pH meter with Automatic Temperature Compensating (ATC) probe. The pH meter is capable of reading to 0.001 pH unit. After each usage the electrode should be washed free from the sample solution with water. Remove any excess water by wiping with a tissue, such as Kimwipes or equivalent. When the electrode is not in use, keep the electrode tip immersed in pH 7 buffer solution or electrode storage solution. Equipment details are as follows:

pH Meter: Meter capable of reading to 0.01 or 0.001 pH units.

Electrode: Orion Ross Sure-Flow combination: Glass body—VWR #34104-834/Orion #8172BN or VWR#10010-772/Orion #8172BNWP.

Epoxy body—VWR #34104-830/Orion #8165BN or VWR#10010-770/Orion #8165BNWP.

Semi-micro, epoxy body—VWR #34104-837/Orion #8175BN or VWR#10010-774/Orion #3175BNWP.

Orion PerpHect combination: VWR #34104-843/Orion #8203BN semi-micro, glass body.

ATC Probe: Fisher Scientific, Cat. #13-620-16.

pH Buffering Agent

The oral care compositions herein may include an effective amount of a buffering agent or pH trimming agents, as used herein, refer to agents that can be used to adjust the pH of the oral care compositions to the above-identified pH range. The buffering agents include alkali metal hydroxides, ammonium hydroxide, organic ammonium compounds, carbonates, sesquicarbonates, borates, silicates, phosphates, imidazole, and mixtures thereof.

Specific buffering agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid.

In one embodiment, 0.01% to 3%, preferably from 0.1% to 1% of TSP by weight of the composition, and 0.001% to 2%, preferably from 0.01% to 0.3% of monosodium phosphate by weight of the composition is used. Without wishing to be bound by theory, TSP and monosodium phosphate may have calcium ion chelating activity and therefore provide some monofluorophosphate stabilization (in those formulations containing monoflurophospahte).

Water

The term "orally acceptable carrier" as used herein means a liquid or semi-solid vehicle such as a paste or a gel for containing the active ingredients of the present invention and delivering them to the oral cavity. Water is commonly used as a carrier material in oral compositions due to its many benefits. For example, water is useful as a processing aid, is benign to the oral cavity and assists in quick foaming of toothpastes. Water may be added as an ingredient in its own right or it may be present as a carrier in other common raw materials such as, for example, sorbitol and sodium lauryl sulphate. The term total water content as used herein means the total amount of water present in the oral care composition, whether added separately or as a solvent or carrier for other raw materials but excluding that which may be present as water of crystallization in certain inorganic salts.

The oral care compositions of the present invention comprise at least about 30% of a total water content. In an embodiment, the oral care composition comprises from about 40% to about 70% of a total water content. In other embodiments, the compositions include from about 45% to about 65%, alternatively from about 40% to about 60%, alternatively from about 50% to about 70%, alternatively from about 50% to about 60%, alternatively from about 45% to about 55%, alternatively from about 55% to about 65%, alternatively from about 50% to about 60%, alternatively about 55%, alternatively combinations thereof, of a total water content. Preferably, the water is USP water.

Chelants

The oral care compositions of the present invention comprise one or more chelants, also known as chelating agents. The term "chelant", as used herein means a bi- or multidentate ligand having at least two groups capable of binding to stannous ions and preferably other divalent or polyvalent metal ions and which, at least as part of a chelant mixture, is capable of solubilising the stannous ions and other optional metal ions within the oral care composition. Groups capable of binding to stannous and other metal ions include carboxyl, hydroxl and amine groups. Typically, those chelants useful herein will also form water soluble stable complexes with the stannous ions.

Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; salts thereof and mixtures thereof. The chelants can also be a polymer or copolymer in which the chelating ligands are on the same or adjacent monomer.

Preferred chelant polymers are polyacids selected from the group consisting of a homopolymer of a monomer, a co-polymer of two or more different monomers, and a combination thereof wherein the monomer or at least one of the two or more different monomers is selected from the group consisting of acrylic acid, methacrylic acid, itaconic acid, maleic acid, glutaconic acid, aconitic acid, citraconic acid, mesaconic acid, fumaric acid and tiglic acid.

Particularly preferred is a methylvinylether/maleic acid (PVM/MA) copolymer. Also suitable are tripolyphosphates. Longer chain linear polyphosphates, though good chelants, are susceptible to hydrolysis in aqueous compositions. Upon hydrolysis they form Olihophosphates which form insoluble zinc complexes. In one embodiment the composition comprises less than 0.1% of polyphosphates having a chain length of four or more.

Preferred organic acid chelants herein comprise citrate, malate, tatirate, gluconate, succinate, lactate, malonate, maleate, and mixtures thereof, whether added in their free acid or salt forms.

Abrasives

Dental abrasives are useful in oral care compositions for their ability to remove surface stains and pellicle and for polishing the teeth. The oral care compositions of the present invention may contain a dental abrasive. Dental abrasives useful in the oral care composition of the subject invention include many different materials. The material selected must be one which is compatible with the composition of interest and does not excessively abrade dentin. Suitable abrasives include, for example, silicas including gels and precipitates, fused silica, insoluble sodium polymetaphosphate, hydrated alumina, and resinous abrasive materials such as particulate condensation products of urea and formaldehyde.

Silica dental abrasives of various types are preferred herein because of their unique benefits of exceptional dental cleaning and polishing performance without unduly abrading tooth enamel or dentine. Silica abrasive polishing materials herein, as well as other abrasives, generally have an average particle size ranging from 0.1 to 30 µm, and preferably from 5 to 15 µm. The abrasive can be precipitated silica or silica gels such as the silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in U.S. Pat. Nos. 4,340,583; 5,603,920; 5,589,160; 5,658,553; 5,651,958; and 6,740,311.

Alternatively, mixtures of dental abrasives can be used, such as mixtures of the various grades of Zeodent® silica abrasives as listed above, or mixtures of the silica abrasives and calcium-containing abrasives. Dental solution, mouth spray, mouth wash, and non-abrasive gel compositions of the subject invention typically contain little or no abrasive.

Sweetener

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral care compositions at levels of from 0.005% to 5%, alternatively 0.01% to 1%, by weight of the composition, alternatively from 0.1% to 0.5%, alternatively combinations thereof.

Fluoride Ion Source

The oral care active may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from 0.0025% to 5% by weight of the composition, alternatively from 0.005% to 2.0% by weight of the composition, to provide anti-caries effectiveness. Examples of suitable fluoride ion-yielding materials are disclosed in U.S. Pat. Nos. 3,535,421, and 3,678,154.

Representative fluoride ion sources include: stannous fluoride, sodium fluoride, potassium fluoride, amine fluoride, sodium monofluorophosphate, zinc fluoride, and mixtures thereof. In one embodiment the oral care composition contains a fluoride source selected from stannous fluoride, sodium fluoride, and mixtures thereof. In on embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

Anti-Calculus Agent

The oral care compositions may include an effective amount of an anti-calculus agent, which in one embodiment may be present from 0.05% to 50%, alternatively from 0.75% to 25%, alternatively from 0.1% to 15%. Non-limiting examples include those described in U.S. Publication No. 2011/0104081A1 at paragraph 64, and those described in U.S. Publication No. 2012/0014883A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Surfactant

The compositions herein may include a surfactant. The surfactant may be selected from anionic, nonionic, amphoteric, zwitterionic, cationic, betaine surfactants, or mixtures thereof. The oral care composition may include a surfactant at a level of from about 0.1% to about 50%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference.

Humectants

The oral care compositions herein may contain humectants. The humectants serves to keep the oral care composition from hardening upon exposure to air, to give a moist feel to the mouth, and, for particular humectants, to impart a desirable sweetness of flavor.

Suitable humectants for the present invention include edible polyhydric alcohols such as glycerin, sorbitol, xylitol, butylene glycol, polyethylene glycol, propylene glycol, and combinations thereof. In one embodiment, the humectant is selected from sorbitol, glycerin, and combinations thereof. In yet another embodiment, the humectants is sorbitol. In one embodiment, the oral care composition comprises from 20% to less than 80% of humectants by weight of the composition, preferably from 30% to 50%. In yet another embodiment, the oral care composition contains 30% to 50% of sorbitol by weight of the oral care composition.

Coloring Agents

The oral care compositions herein may include a coloring agent (i.e., pigments, dyes and opacifiers). The coloring agent may be in the form of an aqueous solution, preferably 1% coloring agent in a solution of water. Titanium dioxide may also be added to the present composition. Titanium dioxide is a white powder which adds opacity to the oral care compositions. Titanium dioxide generally comprises from about 0.25% to about 5%, by weight of the oral care composition.

Flavorant

The oral care compositions herein may include from about 0.001% to about 5%, alternatively from about 0.01% to about 4%, alternatively from about 0.1% to about 3%, alternatively from about 0.5% to about 2%, alternatively combination thereof, of a flavorant composition by weight of the oral care composition. The term flavorant composition is used in the broadest sense to include flavor ingredients, or sensates, or sensate agents, or combinations thereof. Flavor ingredients may include those described in U.S. Publication No. 2012/0082630A1 at paragraph 39; and sensates and sensate ingredients may include those described at paragraphs 40-45, incorporated herein by reference.

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the consumer. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide (known commercially as "WS-3"). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxy-propane-1,2-diol, isopulegol, p-menthane-3,8-diol; menthone glycerine acetal (known commercially as "MGA"); menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3 (2H)-furanone (DMPF); icilin (also known as AG-3-5, chemical name 142-hydroxyphenyl]-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

The oral care compositions herein can further include herbal ingredients such as extracts of chamomile, oak bark, Melissa, rosemary and salvia. These, and some of the herb-derived flavoring components can be included at levels just sufficient to provide a contribution to the flavor or they can be added at higher levels, such as 1% or more, in order to provide a greater therapeutic effect.

Other suitable flavorant components are described in Fenaroli's *Handbook of Flavor Ingredients*, Third Edition, Volumes 1 & 2, CRC Press, Inc. (1995), and Steffen Arctander's *Perfume and Flavour Chemicals*, Volumes 1 & 2 (1969).

Other Ingredients

The present oral care composition can comprise the usual and conventional ancillary components such as anti-microbial agents, fluoride ions, and other ingredients that are known to one skilled in the art. It will be appreciated that selected components for the oral care compositions must be chemically and physically compatible with one another.

Method of Use

The present invention also relates to methods for treating the oral cavity comprising administering to the oral care cavity an oral care composition according to the present invention. In an embodiment, the term "treating" refers to cleaning and polishing teeth. The method of use herein comprises contacting a subject's dental enamel surfaces and oral mucosa with the oral care compositions according to the present invention. The method of treatment may be by brushing with a dentifrice or rinsing with a dentifrice slurry or mouthrinse. Other methods include contacting the topical oral gel, mouthspray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral care composition may be used as frequently as toothpaste, or may be used less often, for example, weekly, or used by a professional in the form of a prophy paste or other intensive treatment.

Test Methods

It is understood that the assays disclosed in the Test Methods section of the present application must be used to determine the respective values of the parameters of the present invention, as such an invention is described and claimed herein.

1. Tip Viscosity Assay

This assay is used to measure the viscosity of the oral care composition near the tip of the dispenser in which it is contained (also referred to as 'Tip Viscosity'). The Tip Viscosity is relevant to the determination of phase stability property of a formulation over time. According to this method, the Tip Viscosity of the oral care compositions can be measured via a control rate model using a Thermo HAAKE MARS Rotational Rheometer with spindle and a 20 mm diameter parallel-plate with the following parameters: a gap of approximately 1.0 mm, shear rates of 0.1 l/s to 100 l/s, at temperature of 25° C. The details of the method are as follows:

Sample Preparation:

Samples of the oral care composition are prepared as follows.
1. Pack about 90 grams of the composition into a 180 grams transparent plastic laminate tube having a diameter of 38 mm and a height of 177.5 mm, and seal the opening (i.e., tail).
2. Place the tube in the vertical position with the tail positioned up and incubate the samples at 40° C. for varying duration (e.g., 0, 1 month, 2 months, 3 months, 4.5 months, etc.). The Tip Viscosity measurement is based on the average of tripilicate tubes for each sampling time point.
3.
Measurement:
4. After the incubation, use scissors to cut the tube near the middle to give approximately equal halves (i.e., upper & lower portions of the tube). Try to avoid touching the packed composition in the upper portion of the tube.
5. Use a spatula to load about 0.4 g of the packed composition from the upper portion of the tube onto the bottom plate of the Rheometer.
6. Lift the upper plate to standby position at 6.000 mm, then lift the upper plate to position at 1.040 mm in 60 secs.
7. Trim samples of the oral care composition with plastic strip and attach the anti-evaporation cap.
8. Lift the upper plate to measuring position at 1.000 mm and re-set the normal force. Set the temperature at 25° C., then standby at 25° C. for 300 secs.
9. Continuous rotation ramp measurement recorded using control rate model with parameters: shear rate from 0.1 l/s to 100 l/s; data point 150 with log distribution; test duration 300 secs.
10. Record Tip Viscosity result at shear rate of 1 $s^{-1}$ as integer.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example 1

Toothpaste compositions according to the present invention ("Present Invention Sample 1") and a comparative formulation ("Comparative Sample 1") are shown below with amounts of components in wt %. These compositions are made using conventional methods.

TABLE 1

Oral Care Formulations

| | Amount (Wt %) | |
|---|---|---|
| Ingredients | Present Invention Sample 1 | Comparative Sample 1 |
| Stannous Chloride | 1.16 | 1.16 |
| Phytic Acid | — | 0.8 |

TABLE 1-continued

Oral Care Formulations

| Ingredients | Amount (Wt %) | |
|---|---|---|
| | Present Invention Sample 1 | Comparative Sample 1 |
| Sorbitol | 48.0 | 38.07 |
| Sodium Carboxymethyl Cellulose | — | 1.3 |
| Carrageenan | 1.5 | 0.7 |
| Xanthan Gum | 0.88 | — |
| Hydroxyethyl Cellulose | — | 0.5 |
| Water and minors (e.g., color soln.) | q.s. | q.s. |
| Target pH | 6 | 6 |

Example 2

Phase Stability

Figure 2:
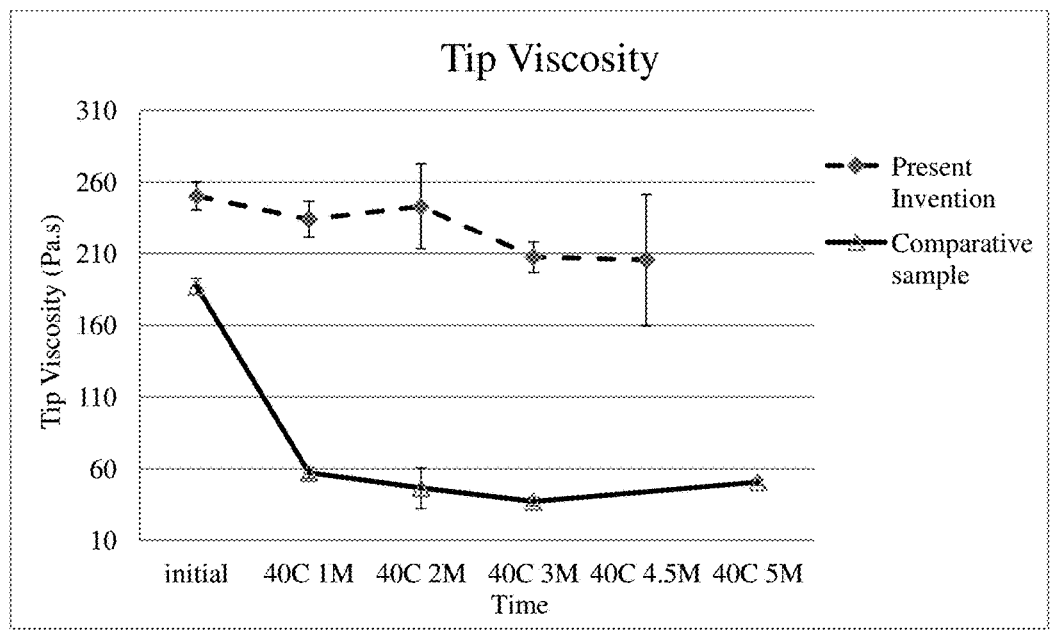
FIG. 2 shows the Tip Viscosity over time for a sample oral care formulation of the present invention versus a comparative sample.

In order to determine phase stability over a period time for the oral care composition of the present invention, a Tip Viscosity assay was carried out which compared a sample composition with carrageenan, and xanthan gum (but no CMC) versus a comparative formulation containing carrageenan, hydroxyethyl cellulose and CMC (but no xanthan gum). Tip Viscosity was measured for the formulations from time 0 to 5 months stored at 40° C. As shown in FIG. 2, the Tip Viscosity for the Comparative Sample drops quickly after 1 month while the Sample 1 composition of the present invention remains relative consistent up to 4.5 months. Additionally, the Sample 1 composition also shows no visual phase separation by 4.5 months.

Example 3

Toothpaste Formulations

The following examples in Table 2 further describe and demonstrate the use of the present invention within toothpaste embodiments. These examples are given solely for the purpose of illustration and are not to be construed as limitations of the present invention as many variations thereof are possible. Toothpaste compositions are shown below with amounts of components in weight %. These compositions are made using conventional methods.

TABLE 2

Toothpaste Formulations

| Ingredient | Example A (wt %) | Example B (wt %) | Example C (wt %) | Example D (wt %) |
|---|---|---|---|---|
| Sorbitol sol. (70%) | 48.000 | 48.000 | 38.000 | 48.000 |
| Sodium Fluoride | 0.321 | 0.210 | 0.321 | — |
| Zinc Citrate | — | 0.533 | 0.533 | — |
| Zinc Lactate Dihydrate | 1.850 | — | — | 1.070 |
| Stannous Chloride Dihydrate | 1.160 | 1.160 | 1.160 | 0.510 |
| Stannous Fluoride | — | — | — | 0.454 |
| Na Gluconate | 1.064 | 1.064 | 1.064 | 1.064 |
| Xanthan Gum | 0.875 | 0.300 | 1.000 | 0.875 |
| Carrageenan | 1.500 | 1.500 | 0.65 | 1.500 |
| Silica Abrasive | 16.000 | 20.000 | 17.000 | 16.000 |
| Sodium Lauryl Sulfate (28% soln.) | 7.000 | 5.000 | 7.500 | 7.000 |
| Na Saccharin | 0.300 | 0.300 | 0.250 | 0.300 |
| Flavor | 1.100 | 1.000 | 1.300 | 1.100 |
| Na Hydroxide (50%) | 0.980 | 0.980 | 0.900 | 0.650 |
| Water and minors (e.g. color soln.) | q.s. | q.s. | q.s. | q.s |
| Target pH | 6.0 | 6.0 | 6.0 | 6.0 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a. from 0.01% to 2% by weight of a stannous chloride source;
   b. a thickening agent consisting of:
      i) from 1% to 5% by weight carrageenan; and
      ii) from 0.3% to 0.875% by weight xanthan gum;
   c. at least 30% by weight of a total water content; and
   d. from 20% to 80% of a humectant selected from the group consisting of glycerin, sorbitol, xylitol, butylene glycol, polyethylene glycol, propylene glycol, and combinations thereof;
   e. a dental abrasive consisting of precipitated silica;
   f. from 0.01% to 2% by weight of a fluoride ion source;
   wherein the composition has a pH of greater than 4 and comprises less than 0.001% of a charged cellulose derivative having greater than 0.5 charged groups per sugar residue unit along the polysaccharide backbone;
   wherein the composition has a Tip Viscosity of greater than 100 Pa·s after 4.5 months at 40° C.;
   wherein the xanthan gum has a degree of substitution of less than 0.4 carboxylate groups per sugar residue.

2. The oral care composition according to claim 1, wherein the charged cellulose derivative is carboxymethyl cellulose (CMC).

3. The oral care composition according to claim 1, wherein the stannous chloride is selected from the group consisting of stannous chloride dehydrate, stannous chloride anhydrous, and combinations thereof.

4. The oral care composition according to claim 1, wherein the carrageenan is present in the amount of from 0.7% to 2% by weight.

5. The oral care composition according to claim 4, wherein the carrageenan is selected from the group consisting of Kappa-carrageenan, Iota-carrageenan, Lambda carrageenan, and combinations thereof.

6. The oral care composition according to claim 5, wherein the carrageenan is Iota-carrageenan.

7. The oral care composition according to claim 1, wherein the pH is between 4.5 and 9.5.

8. The oral care composition according to any claim 7, wherein the pH is between 5 and 7.

9. The oral care composition according to claim 1, wherein the total water content is between 30% to 60% by weight.

10. The oral care composition according to claim 1, further comprising 0.1% to 10% by weight of a chelant.

11. The oral care composition according to claim 10, wherein the chelant is selected from the group consisting of a lactate, citrate, gluconate, and combinations thereof.

12. The oral care composition according to claim 1, wherein the Tip Viscosity does not substantially decrease after 4 months at 25° C.

13. A method for treating the oral cavity comprising administering to the oral cavity an oral care composition according to claim 1.

14. An oral care composition comprising:
   a. from 0.01% to 2% by weight of stannous chloride;
   b. a thickening agent consisting of:
      i) from 1.25% to 3% by weight carrageenan; and
      ii) from 0.3% to 0.875% by weight xanthan gum;
   c. at least 30% by weight of a total water content; and
   d. from 20% to 80% of a humectant selected from the group consisting of glycerin, sorbitol, xylitol, butylene glycol, polyethylene glycol, propylene glycol, and combinations thereof;
   e. a dental abrasive consisting of precipitated silica;
   f. from 0.01% to 2% by weight of stannous fluoride;
   wherein the composition has a pH of greater than 4 and comprises less than 0.001% of a charged cellulose derivative having greater than 0.5 charged groups per sugar residue unit along the polysaccharide backbone.

* * * * *

UNITED STATES PATENT AND TRADEMARK OFFICE
CERTIFICATE OF CORRECTION

PATENT NO. : 10,213,368 B2
APPLICATION NO. : 14/633389
DATED : February 26, 2019
INVENTOR(S) : Xiaoxiao Li et al.

Page 1 of 1

It is certified that error appears in the above-identified patent and that said Letters Patent is hereby corrected as shown below:

On the Title Page

In the Inventors section, please delete "Andrew Frederic Broth" and insert -- Andrew Frederic Groth --.

Signed and Sealed this
Second Day of July, 2019

Andrei Iancu
*Director of the United States Patent and Trademark Office*